United States Patent
Doan et al.

(10) Patent No.: US 6,766,203 B2
(45) Date of Patent: Jul. 20, 2004

(54) BODY IMPLANTABLE LEAD WITH IMPROVED TIP ELECTRODE ASSEMBLY

(75) Inventors: Phong D. Doan, Stevenson Ranch, CA (US); John R. Helland, Saugus, CA (US); Yougandh Chitre, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 485 days.

(21) Appl. No.: 09/828,353

(22) Filed: Apr. 5, 2001

(65) Prior Publication Data

US 2002/0147488 A1 Oct. 10, 2002

(51) Int. Cl.$^7$ ................................................ A61N 1/18
(52) U.S. Cl. ...................................................... 607/122
(58) Field of Search ............................... 600/372–374, 600/377, 393; 607/116, 119, 120, 122

(56) References Cited

U.S. PATENT DOCUMENTS

| | | | |
|---|---|---|---|
| 4,506,680 A | 3/1985 | Stokes ........................ 128/786 |
| 4,844,099 A | 7/1989 | Skalsky et al. ............. 128/785 |
| 5,324,324 A | 6/1994 | Vachon et al. .............. 607/120 |
| 5,408,744 A | 4/1995 | Gates .......................... 29/875 |
| 5,496,360 A | * 3/1996 | Hoffmann et al. .......... 607/120 |
| 5,569,883 A | 10/1996 | Walter et al. ............. 174/84 R |
| 5,869,804 A | * 2/1999 | Mueller et al. ........ 219/121.64 |
| 5,908,385 A | * 6/1999 | Chechelski et al. ......... 600/374 |
| 6,001,095 A | * 12/1999 | de la Rama et al. .......... 606/41 |

* cited by examiner

Primary Examiner—Jeffrey R. Jastrzab
Assistant Examiner—Frances P. Oropeza

(57) ABSTRACT

A body implantable lead assembly adapted to transmit electrical tissue stimulating signals between a proximal end portion of the lead assembly and a distal end portion of the lead assembly includes an electrical conductor extending between the proximal and distal end portions of the lead assembly for transmitting the electrical signals. The conductor has an enlarged, preferably ball shaped distal extremity comprising a termination element. The lead assembly includes a tip electrode having a proximal portion, a proximal extremity, a distal portion and a distal extremity, the distal extremity comprising an active electrode surface. At least the proximal portion of the tip electrode comprises a tubular structure, the tubular proximal portion having an inside diameter slightly smaller than the termination element on the distal extremity of the conductor. The tubular proximal portion of the tip electrode has formed within the wall thereof at least one longitudinally oriented, keyhole-shaped opening. The opening comprises an aperture and a longitudinal slot connecting the aperture and the proximal extremity of the tip electrode, the aperture being smaller than the termination element. The termination element is seated in the aperture of the at least one opening and one or welds may be added between the periphery of the aperture and the termination element to enhance the electrical and mechanical integrity of the connection therebetween.

17 Claims, 5 Drawing Sheets

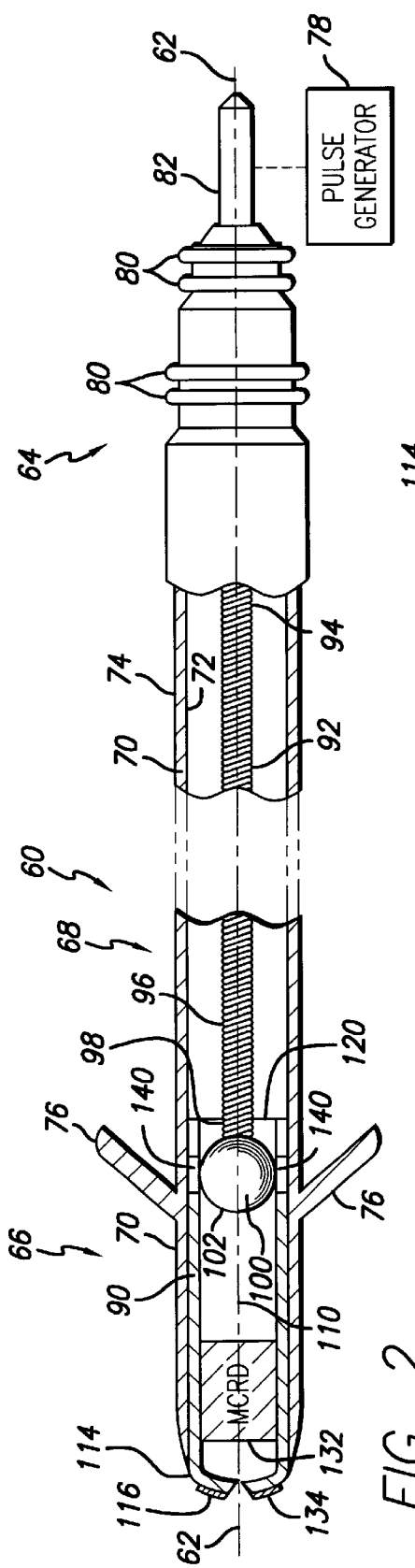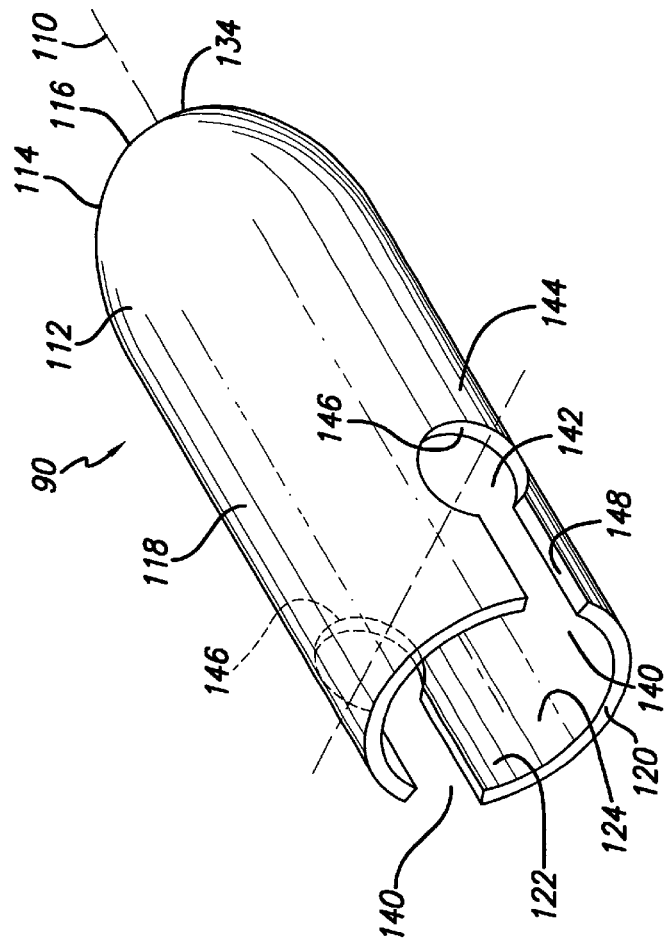
FIG. 2
FIG. 3

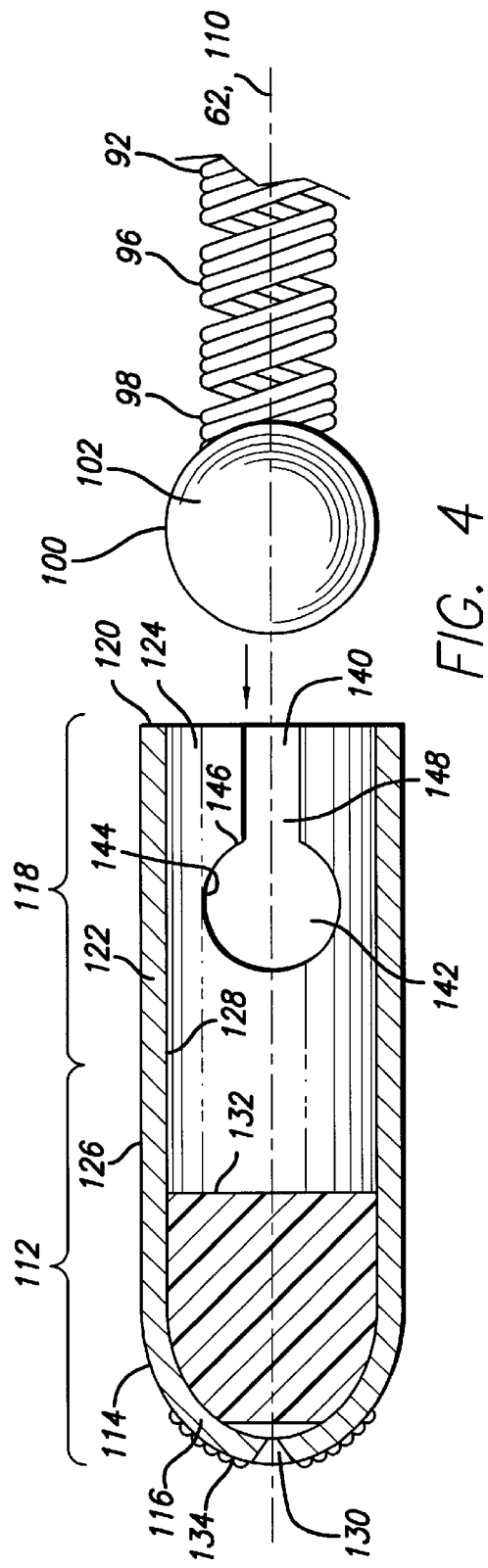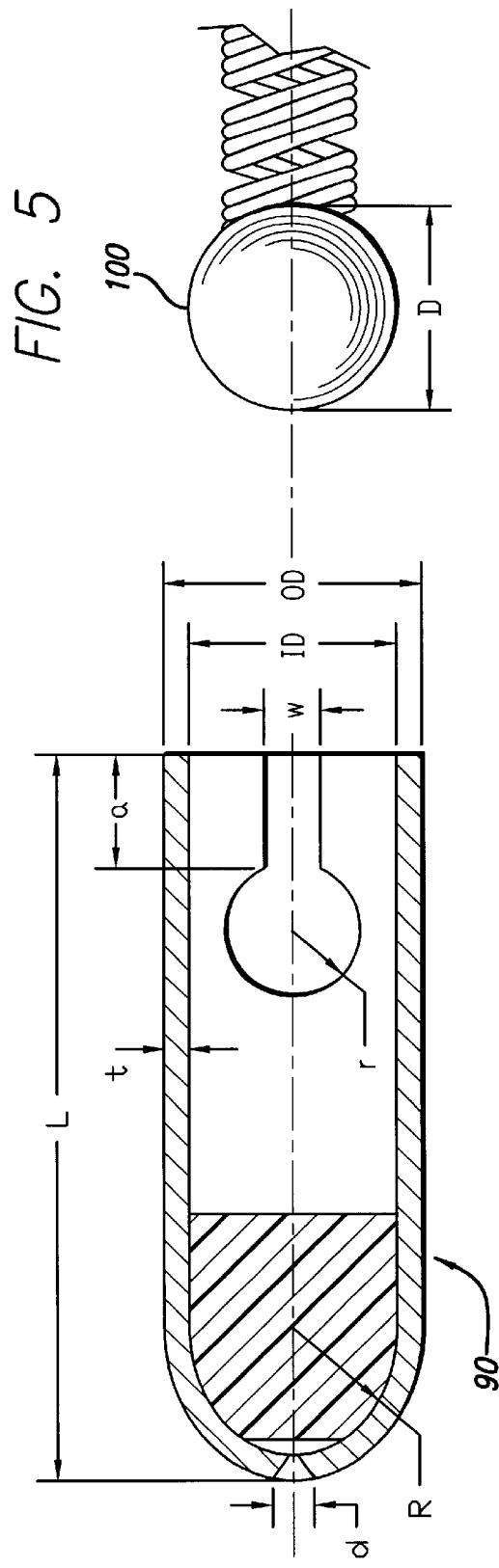

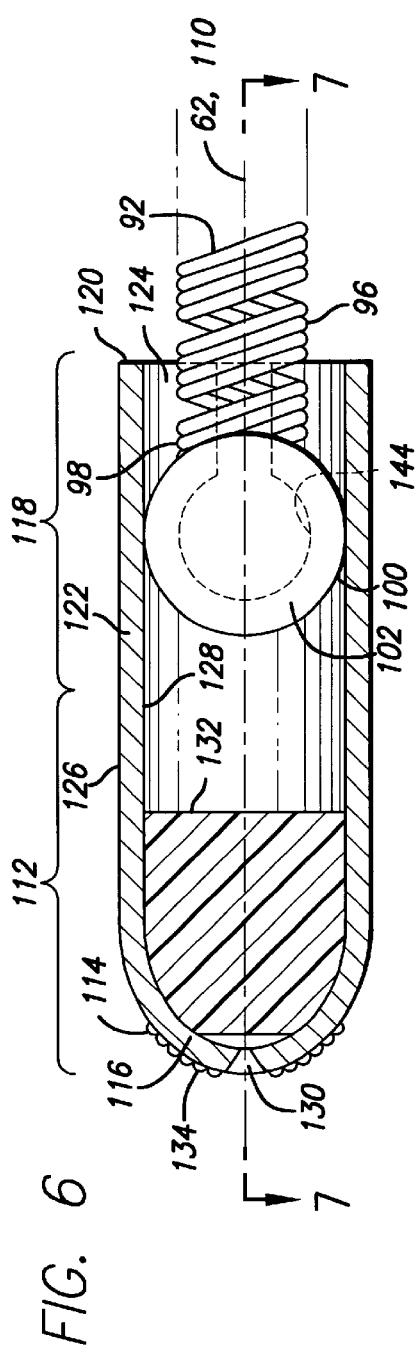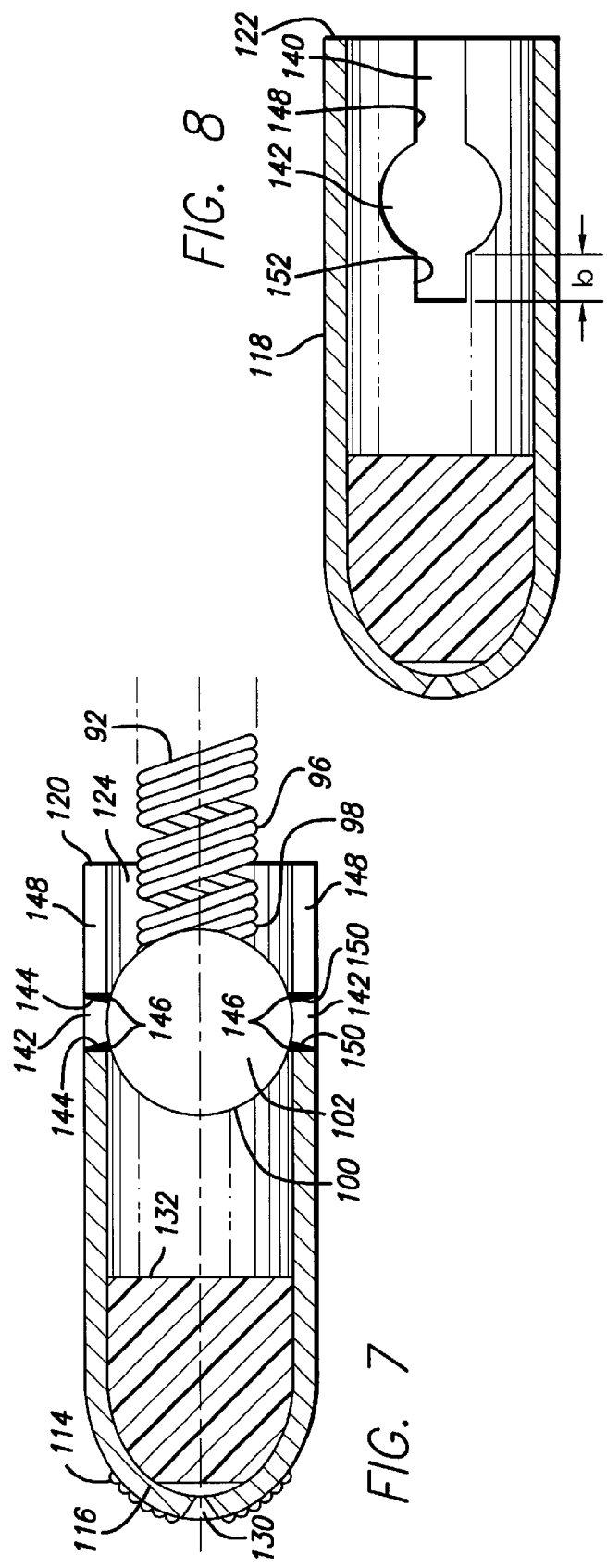

BODY IMPLANTABLE LEAD WITH IMPROVED TIP ELECTRODE ASSEMBLY

FIELD OF THE INVENTION

The present invention relates generally to lead assemblies for coupling implantable pulse generating medical devices with selected body tissue to be stimulated, and particularly, to tip electrodes forming part of such lead assemblies.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pulse generators with the heart may be used for pacing, or for sensing electrical signals produced by the heart and representing cardiac activity, or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end a tip electrode designed to intimately contact the endocardium, the tissue lining the inside of the heart. An epicardial type lead includes a tip electrode in direct contact with the outside of the heart, that is, the epicardium. A myocardial lead has a tip electrode inserted into heart muscle, that is, the myocardium. In one typical form thereof, these leads include a proximal end having a connector pin adapted to be received by a mating socket in the pulse generator. A flexible, conductor, typically having a coiled configuration, is surrounded by an insulating tube or sheath and couples the connector pin at the proximal end of the lead and the tip electrode at the distal end of the lead.

The design of an implantable pacemaker pacing and sensing lead has a significant influence on the cost of its manufacture. For example, conventional pacing/sensing leads typically comprise several individual components which are assembled and welded together in a series of labor- and time-intensive, and therefore costly, steps in order to provide a reliable electrical and mechanical connection between the tip electrode and the associated electrical conductor.

With reference to FIG. 1, there is shown a simplified, axial cross section of an example of a conventional prior art lead assembly in the form of a unipolar, passive endocardial lead assembly 10 including a distal end portion 12. The lead assembly 10 includes an elongated lead body 14 extending along a central longitudinal axis 16 and covered by a tubular, flexible, biocompatible, biostable insulative sheath or housing 18 fabricated of silicone rubber, polyurethane, or other suitable polymer. As is known, the lead assembly's proximal end portion (not shown in FIG. 1) is adapted to be electrically coupled to the receptacle of an implantable tissue stimulation pulse generator or pacemaker by means of a connector including an electrically conductive hollow pin.

At the distal end portion 12 of the lead assembly, the insulative sheath 18 carries a plurality of outwardly extending tines 20 of known design for cooperating with the fibrous myocardial tissue to passively retain a tip electrode 22, comprising part of a tip electrode assembly 24, in position against the endocardium, in a fashion well known in the pacing art. The tip electrode 22 includes a proximal end 26 and a distal end 28, the latter having a distal extremity 29 defining an active tissue stimulating electrode surface 30 which, in the particular example shown, is generally hemispherical in shape. The tip electrode 22 includes a generally tubular section 31 having an interior chamber 32 which extends between the proximal and distal ends 26, 28 of the tip electrode. The distal end 28 of the tip electrode 22 may include one or more grooves 34 extending transversely of the longitudinal axis 16. A central bore 36 provides communication between the grooves 34 and the chamber 32 to form an elution path for the passage of a drug stored in a drug impregnated plug 38 enclosed within the chamber 32 of the tubular section of the tip electrode adjacent the distal end 28 thereof. The drug may be one intended to counter thrombus formation, fibrosis, inflammation or arrhythmias, or any combination thereof, or to accomplish any desired localized purpose. For example, the drug dispensing plug may be loaded with a steroidal anti-inflammatory such as dexamethasone serving to reduce the stimulation threshold by minimizing fibrotic encapsulation or fibrosis. The typical prior art tip electrode assembly 24 shown in FIG. 1 further includes a weld element 40 secured to the proximal end 26 of the tip electrode 22 by resistance or laser welding or the like. The weld element 40 has a first or distal projection 42 extending into the chamber 32 and a second projection 44, longer than the first projection 42, extending proximally. The second projection 44 includes a flange 46 and a tubular portion 48 extending proximally therefrom. The proximally extending tubular portion 48 of the weld element 40 extends into the lumen 50 of a coiled electrical conductor 52 which is held in place by means of a crimp tube 54, welds, or a combination thereof. As is known in the art, the coiled electrical conductor 52 extends through the lead body 14 to the proximal end of the lead assembly and is coupled to the aforementioned, hollow connector pin. Also, as is known in the art, the insertion and placement of the lead assembly 10 into the heart is aided by means of a stylet (not shown) passed through the hollow connector pin and lumen 50 of the conductor coil 52 and into the tubular portion 48 of the weld element 40 to enable the distal end portion 12 of the lead assembly 10 to be positioned at a desired location in the heart.

It will be seen that the prior art tip electrode assembly 24, which includes the weld element 40, comprises a lengthy, rigid structure making difficult the insertion of the lead transvenously into the heart and its maneuvering and placement therein. It will also be appreciated that there are substantial labor and material costs associated with the fabrication of the multiple component tip electrode assembly 24 of the prior art. For example, considerable time must be spent on resistance or laser welders in order to join the various components with the attendant costs of the skilled labor required.

Thus, there continues to be a need for pacemaker leads having tip electrode assemblies that comprise fewer parts, are simpler and less costly to manufacture and are smaller than existing tip electrode assemblies so as to facilitate insertion and placement of the tip electrode within the heart.

SUMMARY OF THE INVENTION

Tip electrodes in accordance with the present invention are extremely easy to manufacture and accordingly very cost effective in comparison to conventional tip electrodes. Indeed, the minimal expense of fabricating tip electrodes with superior electrical characteristics is a primary advantage of the present invention.

A feature of the present invention is the provision of a tip electrode which can be inexpensively manufactured while maintaining the performance achieved by much more expensive electrode designs.

In accordance with one, specific exemplary embodiment of the present invention, there is provided a body implantable lead adapted to transmit electrical signals between a proximal end portion of the lead and a distal end portion of the lead to thereby stimulate selected body tissue and/or sense electrical signals therefrom. The lead extends in a longitudinal direction and includes an elongated electrical conductor extending between the proximal and distal end portions of the lead assembly for transmitting the electrical signals. The conductor has an enlarged distal extremity or termination element. The lead further includes an electrically conductive tip electrode having a distal portion including a distal extremity defining an active exterior electrode surface. The tip electrode further has a proximal portion and a proximal extremity, at least the proximal portion of the tip electrode comprising a longitudinally extending, generally tubular structure having an interior bounded by a wall. The wall defines at least one through-aperture, the at least one through-aperture being smaller than the enlarged termination element at the distal extremity of the conductor. A longitudinal slot extends from the at least one aperture to the proximal extremity of the tip electrode, the enlarged termination element on the distal extremity of the conductor being disposed within the interior of the tube and being seated within the at least one aperture to provide a secure mechanical and electrical coupling between the conductor and the tip electrode. This coupling is preferably enhanced by laser welding the periphery of the at least one through-aperture to the enlarged termination element on the distal extremity of the conductor. Pursuant to one alternative embodiment of the present invention, the longitudinal slot extends distally from the at least one aperture.

In accordance with another embodiment of the present invention, the wall of the tubular portion of the tip electrode defines two through-apertures, the apertures being substantially diametrically opposed. In this embodiment, a longitudinal slot preferably extends from each of the apertures to the proximal extremity of the tip electrode. Further, each of the longitudinal slots may extend distally from the associated aperture. To enhance the mechanical and electrical coupling between the tip electrode and conductor, the enlarged termination element on distal extremity of the conductor may be welded to the tubular portion of the tip electrode along the periphery of at least one of the two through-apertures.

A drug dispensing element or monolithic controlled release device (MCRD) may be carried within the distal portion of the tip electrode for storing a drug to be dispensed to the body tissue. Such a drug dispensing member preferably takes the form of a plug adapted to be loaded with, for example, a steroidal anti-inflammatory such as dexamethasone which serves to reduce the stimulation threshold by minimizing fibrosis.

From the foregoing, it will be appreciated that the present invention provides an implantable lead having a tip electrode and tip electrode/conductor assembly that are easy and cost effective to manufacture. Moreover, the tip electrode of the invention, because it effectively eliminates the weld element and related structure of the prior art, has a reduced length thereby facilitating its insertion, maneuverability and placement within the heart.

BRIEF DESCRIPTION OF THE DRAWINGS

Further objects, features and advantages of the invention will become apparent from the Detailed Description of the Preferred Embodiments, below, when read in conjunction with the accompanying drawings, in which:

FIG. 2 is a simplified side view, partly in cross section, of an endocardial pacing lead assembly including a tip electrode assembly in accordance with a first exemplary embodiment of the present invention;

FIG. 3 is a perspective view of the tip electrode comprising part of the lead assembly shown in FIG. 2, showing certain details of the tip electrode;

FIG. 4 is a side elevation view, in cross section, of the tip electrode of FIGS. 2 and 3 and a conductor coil assembly adapted to be coupled to the tip electrode;

FIG. 5 is a side elevation view, in cross section, of the tip electrode and conductor coil assembly shown in FIG. 4, with dimensions in accordance with one specific, exemplary form of the invention indicated thereon;

FIG. 6 is a side elevation view, in cross section, of the tip electrode assembly of FIGS. 2–4, showing the tip electrode coupled to the distal extremity of the electrical conductor coil;

FIG. 7 is a cross section view of the tip electrode of the present invention as seen along the line 7—7 in FIG. 6;

FIG. 8 is a cross section view of the tip electrode of the present invention in accordance with a second embodiment thereof;

DETAILED DESCRIPTION OF THE PREFERRED EMBODIMENTS

Figure 1:
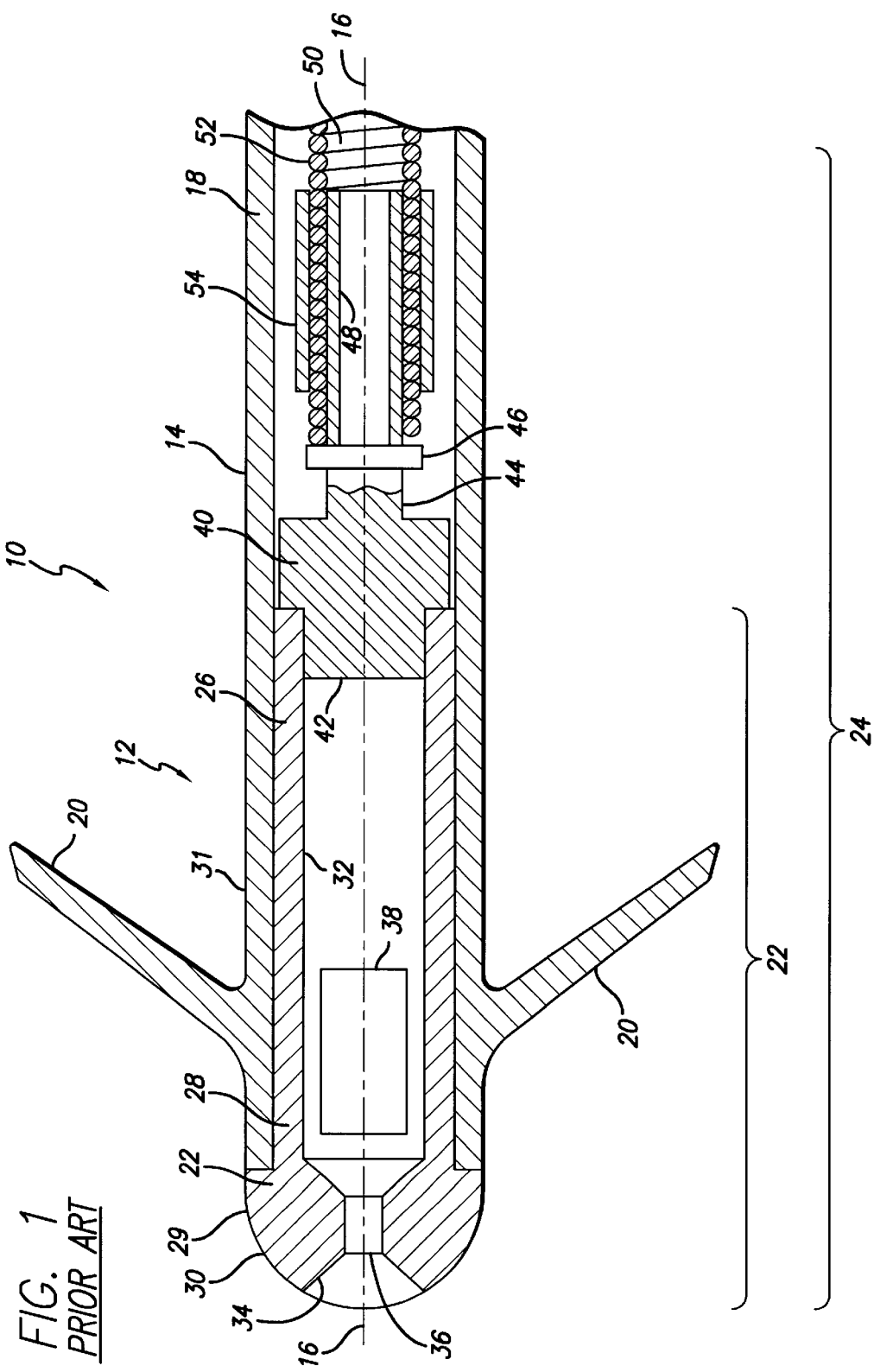
FIG. 1 is a simplified side view, partly in cross section, of an endocardial tip electrode assembly in accordance with the prior art.

The following description presents the preferred embodiments of the invention representing the best modes contemplated for practicing the invention. This description is not to be taken in a limiting sense but is made merely for the purpose of describing the general principles and features of the invention whose scope is defined by the appended claims. Moreover, the contexts in which the invention is shown and described herein, that is, specific implantable, passive, unipolar pacing and sensing leads, are illustrative only; it will be understood by those skilled in the art that the invention may be used in a wide variety of unipolar, bipolar, multipolar and other body implantable tissue stimulating leads, including leads having active, screw-in fixation electrodes in the form of extendable helices.

In this description, the term "distal" refers to a direction toward, or a position closer to, the active or stimulating surface of the tip electrode, and the term "proximal" refers to a direction toward, or a position closer to, the end of the lead assembly that is adapted to be connected to the pulse generator.

Referring now to FIG. 2, there is shown in simplified form a first, specific, exemplary embodiment of the invention comprising a unipolar, endocardial pacing and sensing lead assembly 60 having a longitudinal axis 62, a proximal end portion 64, a distal end portion 66 and an intermediary portion or lead body 68 connecting the proximal and distal end portions 64 and 66. The lead body 68 is covered by a flexible, tubular insulative housing or sheath 70 made of a material such as polyurethane, silicone rubber, or similar biocompatible, biostable elastomeric polymer. The sheath 70 has an interior surface 72 and an exterior surface 74 from which a plurality of tines 76 extend outwardly. The proximal end portion 64 of the lead assembly 60 is adapted to be plugged into a socket or receptacle of a pulse generator 78 and for this purpose the elastomeric sheath 70 includes longitudinally spaced sets of annular ribs 80 for engaging the wall of the pulse generator receptacle so as to seal the receptacle against the entry of body fluids. The proximal end portion 64 of the lead assembly 60 further includes an electrical connector pin 82. As is well known, the pin 82 is adapted to engage a corresponding terminal within the receptacle of the pulse generator 78. The distal end portion 66 of the lead assembly 60 includes a tip electrode 90 for engaging the tissue to be stimulated, in this case, the endocardium. The tines 76 engage endocardial tissue and urge the tip electrode 90 into contact with the endocardium in a direction parallel to the longitudinal axis 62.

The lead body 68 encloses a flexible electrical conductor 92, typically in the form of an elongated (noncoiled) cable or a coil fabricated of MP35N alloy or other suitable conductive material, having a proximal end 94 electrically connected to the connector pin 82 and a distal end 96 electrically coupled to the tip electrode 90 in a manner to be explained. As is well known in the art, the conductor 92 may be multifilar for decreased elongation, increased tensile strength and redundancy to provide continued stimulation and sensing in the event one of the conductor strands breaks. Further, the connector pin 82 on the proximal end portion of the lead assembly is preferably hollow so that in accordance with well known implantation techniques a stylet may be passed through the hollow connector pin 82 and, where the conductor 92 comprises a coiled structure, through the central channel or lumen thereof to enable the implanting physician to maneuver the distal end portion 66 of the lead assembly 60 to position the tip electrode 90 under fluoroscopy to a desired location in the heart.

The elongated electrical conductor 92 extending between the proximal and distal end portions 64 and 66 of the lead assembly 60 transmits electrical signals bidirectionally between the tip electrode 90 and the pulse generator 78. The electrical conductor 92 has a distal extremity 98 provided with a termination element 100 for purposes to be described. The termination element 100 comprises an enlargement on the distal extremity 98 of the conductor 92 which enlargement preferably has a generally ball-like or spherical form 102 with a diameter larger than the width or diameter of the electrical conductor 92 and, in accordance with a preferred form of the invention, is fabricated integrally with the conductor 92 and centered thereon. For example, the distal extremity 98 of the conductor 92 may be heated sufficiently to melt the distal extremity 98 and to allow a molten drop of the conductor material to form which, when solidified, forms the termination element 100. Alternatively, a mass in the form, for example, of a ball or bead of electrically conductive material that is compatible with that of the electrical conductor 92, may be securely attached to the distal extremity 98 of the conductor by, for example, resistance or laser welding. Forming the termination element 100 by heating and melting the distal extremity 98 of the electrical conductor is preferred since it provides the structural integrity, conductive properties and low cost that is a primary object of the present invention. Thus, the termination element 100 may be formed by melting the distal extremity of the conductor 92 by thermal means such as a laser hydrogen flame.

Referring now also to FIGS. 3–7, the tip electrode 90 of the first embodiment is preferably in the form of a tube having a longitudinal central axis 110 that coincides with the longitudinal axis 62 of the lead. The tip electrode 90 includes a distal portion 112 having a distal extremity 114 defining an active or stimulating exterior electrode surface 116 and a proximal portion 118 terminating in a proximal extremity 120. The tip electrode 90 has a wall 122 bounding an interior cavity or bore 124 and the wall 122 includes an outer surface 126 and an inner surface 128. As seen in FIG. 2, the tip electrode 90 is enclosed within the insulating sheath 70 except for the distal extremity 114 of the electrode.

The tip electrode 90 may be made of a platinum-iridium alloy or similar biostable, biocompatible, low polarization, conductive material. In the preferred embodiment, the platinum-iridium alloy has a composition of about 90% platinum and about 10% iridium by weight. Equivalent, conductive materials such as stainless steel, MP35N, platinum, titanium, and alloys thereof, and vitreous carbon, all well known in the pacing art, may be used.

The exposed stimulating electrode surface 116 defined by the distal extremity 114 of the tip electrode has a generally hemispherical shape formed by closing or substantially closing the distal extremity of the tubular tip electrode. In the example under consideration, the distal extremity 114 includes a central opening 130 providing a passage for elution of a drug released from a drug impregnated plug 132 (also known as a monolithic controlled release device or MCRD) as described above in connection with the prior art tip electrode assembly shown in FIG. 1. The use of therapeutic drugs released in vivo to counter trauma caused by an implanted device such as a cardiac pacemaker lead is well known. Such trauma typically occurs in the region in which the distal extremity of the pacing lead tip electrode of the pacing lead contacts the cardiac tissue. Steroid-eluting leads having a tip electrode housing a variety of matrix materials with a drug being stored in, and dispensed from, the tip electrode are also well known. The presence of a steroidal anti-inflammatory, such as dexamethasone, is known to reduce the threshold for stimulation by minimizing fibrotic encapsulation or fibrosis which occurs toward the end of any normal healing response to the implant of an electrode. This minimization of fibrosis allows the electrode and excitable tissue to be in closer proximity, the result of this suppressed foreign body reaction being lower voltage and current requirements at threshold. Thus, steroid eluting tip electrodes can be made smaller than their nonsteroid counterparts and therefore will present higher pacing impedances and afford lower voltage thresholds, minimizing current drain and preserving battery life.

The stimulating or active surface 116 of the tip electrode 90 may be covered with a coating 134 of titanium nitride, platinum black, carbon black, or similar known materials for reducing electrode polarization, to provide Autocapture™ compatibility, and to present a roughened surface adapted to promote tissue ingrowth to help prevent dislodgment of the tip electrode 90. The area of the stimulating or active tip electrode surface 116 preferably ranges from about 1.0 mm² to about 10.0 mm², with a preferred area range of about 3.0 mm² to about 5.0 mm², for providing a pacing impedance in the range of about 600 ohms to about 900 ohms.

In accordance with one specific, exemplary form of the tip electrode of the present invention, the proximal end portion 118 of the tip electrode 90 comprises a split structure. Specifically, formed in the proximal portion 118 of the tip electrode 90 are a pair of diametrically opposed, identical, longitudinally oriented, generally keyhole-shaped openings 140 extending through the wall 122 of the tip electrode 90. Each opening 140 comprises a generally circular aperture 142 defined by a rim or periphery 144 having an inner edge 146, and a longitudinal slot 148 extending from the aperture 142 to the proximal extremity 120 of the tip electrode. Each aperture 142 is smaller than the termination element 100 on the distal extremity of the conductor 92. With reference to FIG. 5, in accordance with the specific embodiment under consideration, the tip electrode 90 and termination element 100 may have the following approximate dimensions, in inches:

L=0.150
OD=0.060
T=0.006
ID=0.048
r=0.0115
w=0.015
D=0.050
a=0.025±0.002
d=0.012/0.016
R=0.030

These dimensions are illustrative only and are not to be taken in any limiting sense.

The tip electrode 90 is coupled to the electrical conductor 92 by inserting the enlarged termination element 100 on the distal extremity of the electrical conductor into the bore 124 of the tubular tip electrode from the proximal extremity 120 thereof and pushing the distal end of the conductor 92 axially toward the distal extremity 114 of the tip electrode. Since the termination element 100 is slightly larger than the inside diameter, ID, of the tubular tip electrode, the split proximal portion 118 of the tip electrode defined by the keyhole shaped openings 140 will tend to slightly flare or deform outwardly elastically. When the termination element 100 on the distal end of the conductor reaches the apertures 140, the termination element snaps into the apertures as the deformed, split end springs back to some extent. With the outer surface 102 of the termination element 100 engaging the inner edges 146 of the apertures 140 so as to be gripped thereby, the termination element is seated in the apertures so as to provide a secure mechanical and electrical coupling. (See FIGS. 6 and 7.) The assembly is completed by joining the inner edge 146 of at least one of the apertures 140 to the termination element 100 by one or more welds 150 further reinforcing the mechanical and electrical integrity of the coupling. It will be seen that this latching or detent coupling design which allows the conductor 92 and tip electrode 90 to be connected by simply pushing them together provides for quick, reliable, easy, low cost assembly of the conductor and tip electrode. Thus, the present invention provides an integrated tip/weld electrode that eliminates the costs associated with assembling and welding together multiple, individual components. Elimination of the weld element 40 of the prior art results in a shorter and therefore more flexible distal end portion of the lead, facilitating its insertion, maneuvering and placement relative to the tissue of the heart.

The traverse cross section shape of the tip electrode 90 is preferably circular but other configurations, such as elliptical, can be used. The tip electrode may be fabricated from tubular or sheet stock, or by molding, casting, machining, or other metal shaping techniques. Although the distal extremity 114 of the tip electrode of the invention preferably has a thin wall, as shown in FIGS. 2–7, the distal extremity may be a solid structure as in the prior art assembly shown in FIG. 1. Although incorporation of a drug impregnated plug such as the plug 132 is preferred, such an element need not be included. For purposes of achieving the primary goals of the invention, it is only necessary that the proximal end portion 118 of the tip electrode be hollow so as to permit formation of at least one, and preferably two, termination element-receiving keyhole-shaped openings 140 in the wall thereof. It will be evident to skilled artisans that more than two keyhole-shaped openings, preferably equiangularly spaced about the central, longitudinal axis, may be provided.

FIG. 8 shows a second embodiment of the present invention similar in all respects to the first embodiment except that the longitudinal slot 148 of the at least one keyhole-shaped opening 140 in the wall 122 of the split tubular proximal portion 118 of the tip electrode includes a longitudinal slot portion 152 extending distally from the aperture 142. As a result of the elongated slot 148, 152, the split proximal portion 118 of the embodiment of FIG. 8 is more readily flexed upon insertion of the enlarged termination element 100 to further facilitate the assembly of the tip electrode 90 and the electrical conductor 92. By way of example and not limitation, the length, b, of the slot portion 152 may range from about 0.001 inch to about 0.040 inch.

Figure 9:
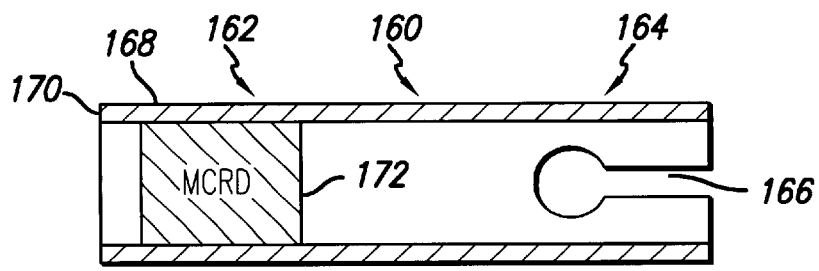
FIG. 9 is a side view, in cross section, of a tip electrode in accordance with a third embodiment thereof.

FIG. 9 is an axial cross section view of a tip electrode 160 in accordance with a third embodiment of the present invention. The tip electrode 160 is in the form of a tube and includes, as in the case of the first embodiment, a distal portion 162 and a proximal portion 164, the latter including at least one longitudinally extending keyhole shaped opening 166 for receiving the enlarged termination element on the distal extremity of a conductor of the kind and in the manner described earlier. The distal portion 162 of the tip electrode 160 terminates at a distal extremity 168 which in the embodiment under consideration comprises simply the open end of the tubular tip electrode structure. The active or stimulating surface of the electrode comprises chiefly the transverse end surface 170 of the tubular structure. A drug impregnated plug or MCRD 172 may be carried within the bore of the tip electrode adjacent the distal extremity 166 thereof.

Figure 10:
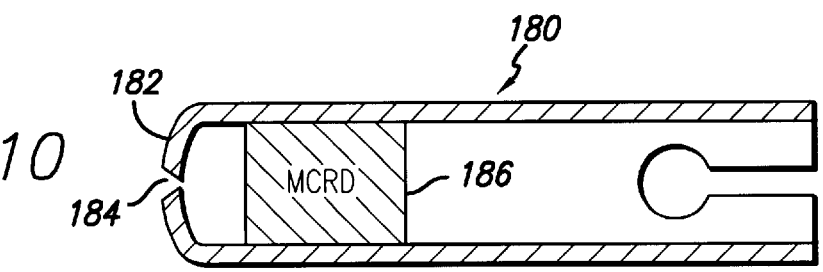
FIG. 10 is a side view, in cross section, of a tip electrode in accordance with a fourth embodiment of the present invention.

FIG. 10 is an axial cross section view of a tip electrode 180 in accordance with a fourth embodiment of the invention. The tip electrode 180 of the third embodiment is similar to that of the first embodiment, except that the distal extremity 182, instead of being generally hemispherical, has a flattened configuration. As in the first embodiment, the distal extremity 182 has a central opening 184 for the passage of a therapeutic drug from a drug impregnated plug 186 that may be included within the distal end portion of the tip electrode 180.

Figure 11:
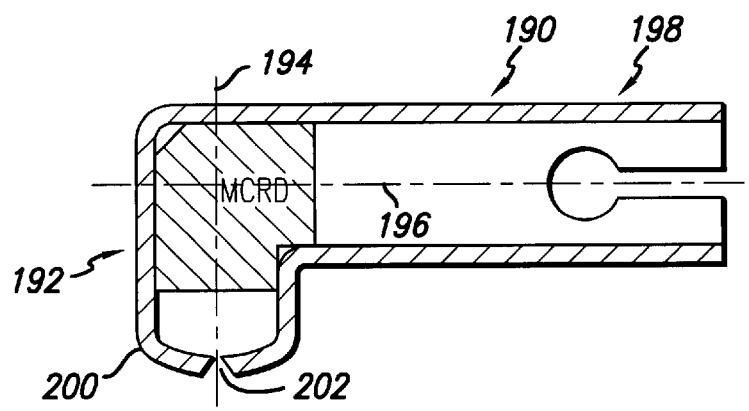
FIG. 11 is a side view, in cross section, of a tip electrode in accordance with a fifth embodiment of the present invention.
Figure 12:
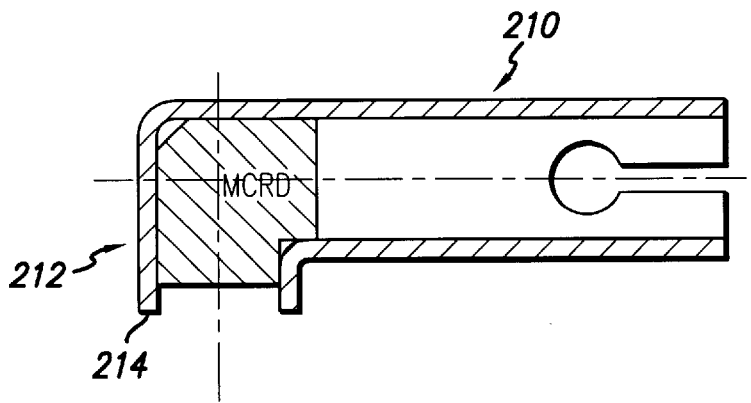
FIG. 12 is a side view, in cross section, of a sixth embodiment of the present invention.

FIGS. 11 and 12 are cross sections of epicardial tip electrodes 190 and 210, respectively, in accordance with fifth and sixth embodiments of the invention. The fourth and fifth embodiments are adapted to be anchored to the outside of the heart, or epicardium, in accordance with techniques well known in the art. The tip electrode 190 of the embodiment of FIG. 11 includes a tubular distal end portion 192 having a central axis 194 disposed perpendicularly to the central axis 196 of the tubular proximal end portion 198 of the tip electrode 190. The distal end portion 192 includes a distal extremity 200 that is closed, except for a central drug passage 202, along the lines of the embodiment of FIG. 10. The tip electrode 210 of the embodiment of FIG. 12 is identical to that of FIG. 11 except that the distal end portion 212 has a distal extremity 214 that is open, similar to the embodiment of FIG. 9.

It should be appreciated that the foregoing description is only illustrative of the invention. Various alternatives and modifications can be devised by those skilled in the art without departing from the spirit of the invention. Accordingly, the present invention is intended to embrace all such alternatives, modifications and variations as fall within the scope of the appended claims.

What is claimed is:

1. A body implantable lead adapted to transmit electrical signals between a proximal end portion of the lead and a distal end portion of the lead and to thereby stimulate selected body tissue and/or sense electrical signals therefrom, the lead extending in a longitudinal direction and comprising:

an elongated electrical conductor extending between said proximal and distal end portions of the lead assembly for transmitting the electrical signals, the conductor having an enlarged distal extremity; and an electrically conductive tip electrode having a distal portion including a distal extremity defining an active exterior electrode surface, the tip electrode further having a proximal portion and a proximal extremity, at least the proximal portion of the tip electrode comprising a longitudinally extending, generally tubular structure having an interior bounded by a wall, the wall defining at least one through-aperture, the at least one aperture being smaller than the enlarged distal extremity of the conductor, a longitudinal slot extending from the at least one aperture to the proximal extremity of the tip electrode, the enlarged distal extremity of the conductor being disposed within the interior of the tube and seated within the at least one aperture.

2. The body implantable lead, as defined in claim 1, in which:

the at least one through-aperture has a periphery; and the enlarged distal extremity of the conductor is welded to the tube along the periphery of the at least one through-aperture.

3. The body implantable lead, as defined in claim 1, in which:

the wall defines two through-apertures, the apertures being substantially diametrically opposed, a longitudinal slot extending from each of the apertures to the proximal extremity of the tip electrode.

4. The body implantable lead, as defined in claim 3, in which:

each of the two through-apertures has a periphery; and the enlarged distal extremity of the conductor is welded to the tube along the periphery of at least one of two through-apertures.

5. The body implantable lead, as defined in claim 1, in which:

the enlarged distal extremity is ball shaped.

6. The body implantable lead, as defined in claim 5, in which:

a diameter of the enlarged distal extremity is greater than an inner diameter of the generally tubular structure.

7. A body implantable lead adapted to transmit electrical signals between a proximal end portion of the lead and a distal end portion of the lead and to thereby stimulate selected body tissue and/or sense electrical signals therefrom, the lead extending in a longitudinal direction and comprising:

an elongated electrical conductor extending between said proximal and distal end portions of the lead assembly for transmitting the electrical signals, the conductor having a diameter and a distal extremity;

a generally ball shaped termination element carried by the distal extremity of the conductor, the ball shaped termination element having a diameter larger than the diameter of the conductor, and an electrically conductive tip electrode having a distal end portion including a distal extremity defining a tissue stimulating exterior electrode surface, the tip electrode further having a proximal end portion and a proximal extremity, at least the proximal portion of the tip electrode comprising a longitudinally extending tube having an interior bounded by a wall, the wall defining at least one through-aperture defined by a rim having a diameter smaller than the diameter of the ball shaped termination element, a longitudinal slot extending from the at least one aperture to the proximal extremity of the tip electrode, the termination element carried by the distal extremity of the conductor being disposed within the proximal portion of the tip electrode in engagement with the rim of the at least one aperture.

8. The body implantable lead, as defined in claim 7, in which:

the at least one through-aperture has a periphery; and the enlarged distal extremity of the conductor is welded to the tube along the periphery of the at least one through-aperture.

9. The body implantable lead, as defined in claim 7, in which:

the wall defines two though-apertures, the apertures being diametrically opposed, a longitudinal slot extending from each of the apertures to the proximal extremity of the tip electrode.

10. The body implantable lead, as defined in claim 9, in which:

each of the two through-apertures has a periphery; and the enlarged distal extremity of the conductor is welded to the tube along the periphery of at least one of two through-apertures.

11. The body implantable lead, as defined in claim 6, in which:

a diameter of the ball shaped termination element is greater than an inner diameter of the interior bounded by the wall.

12. A passive fixation body implantable lead assembly adapted to transmit electrical signals between a proximal end portion of the lead assembly and a distal end portion of the lead assembly and to thereby stimulate selected body tissue and/or sense electrical signals therefrom, the lead assembly having a longitudinal axis and comprising:

an electrical conductor extending between said proximal and distal end portions of the lead assembly for transmitting the electrical signals, the conductor having an enlarged distal end;

a sheath of insulative, biocompatible material enclosing the electrical conductor for electrically insulating the conductor from body tissue and body fluids, the insulative sheath having a distal extremity;

a tip electrode having a proximal portion, a proximal extremity, a distal portion and a distal extremity, the distal extremity comprising an active electrode surface, the tip electrode comprising a generally tubular structure having a wall with at least one longitudinally oriented keyhole-shaped opening therein, the opening comprising an aperture in the proximal portion of the tip electrode and a slot connecting the aperture and the proximal extremity of the tip electrode, the aperture being smaller than the enlarged distal end of the conductor, the enlarged distal end of the conductor being seated in the aperture; and a drug dispensing member disposed with the distal portion of the tubular tip electrode.

13. The body implantable lead assembly, as defined in claim 12, in which:

the at least one through-aperture has a periphery; and the enlarged distal extremity of the conductor is welded to the tube along the periphery of the at least one through-aperture.

14. The body implantable lead assembly, as defined in claim 12, in which:

the wall defines two through-apertures, the apertures being diametrically opposed, a longitudinal slot extending from each of the apertures to the proximal extremity of the tip electrode.

15. The body implantable lead assembly, as defined in claim 14 which:

each of the two through-apertures has a periphery; and the enlarged distal extremity of the conductor is welded to the tube along the periphery of at least one of two through-apertures.

16. The body implantable lead, as defined in claim 12, in which:

the enlarged distal extremity is ball shaped.

17. The body implantable lead, as defined in claim 16, in which: a diameter of the bell shaped termination element is greater than an inner diameter of the tubular structure.

* * * * *